US012008882B2

(12) United States Patent
Pinchasov

(10) Patent No.: US 12,008,882 B2
(45) Date of Patent: Jun. 11, 2024

(54) APPARATUS FOR DETECTION OF DROWNING CONDITIONS

(71) Applicant: Yafim Pinchasov, Holon (IL)

(72) Inventor: Yafim Pinchasov, Holon (IL)

( * ) Notice: Subject to any disclaimer, the term of this patent is extended or adjusted under 35 U.S.C. 154(b) by 216 days.

(21) Appl. No.: 17/564,381

(22) Filed: Dec. 29, 2021

(65) Prior Publication Data

US 2022/0215736 A1 Jul. 7, 2022

Related U.S. Application Data

(60) Provisional application No. 63/133,801, filed on Jan. 5, 2021.

(51) Int. Cl.
| | | |
|---|---|---|
| *G08B 21/08* | (2006.01) | |
| *A61B 5/00* | (2006.01) | |
| *A61B 5/08* | (2006.01) | |
| *A61B 5/107* | (2006.01) | |

(52) U.S. Cl.
CPC .......... *G08B 21/088* (2013.01); *A61B 5/0816* (2013.01); *A61B 5/1071* (2013.01); *A61B 5/6823* (2013.01)

(58) Field of Classification Search
None
See application file for complete search history.

(56) References Cited

U.S. PATENT DOCUMENTS

| 11,724,740 | B2 * | 8/2023 | Cautillo | G01S 15/931 |
| | | | | 701/41 |
| 2013/0269097 | A1 * | 10/2013 | Alammari | E04H 4/065 |
| | | | | 4/495 |
| 2014/0293056 | A1 * | 10/2014 | Popham | G01F 23/804 |
| | | | | 348/148 |
| 2015/0033846 | A1 * | 2/2015 | Tran | G01S 15/02 |
| | | | | 73/304 C |
| 2015/0046071 | A1 * | 2/2015 | Clarke | B60W 10/04 |
| | | | | 701/112 |
| 2015/0066339 | A1 * | 3/2015 | Hoare | G01F 23/804 |
| | | | | 701/116 |
| 2020/0039434 | A1 * | 2/2020 | Sharp | B60Q 9/00 |
| 2020/0039505 | A1 * | 2/2020 | Sharp | B60W 50/14 |
| 2020/0311953 | A1 * | 10/2020 | Olshansky | G03B 15/00 |
| 2021/0166568 | A1 * | 6/2021 | Kersulec | B63B 43/18 |
| 2021/0171043 | A1 * | 6/2021 | Altman | G01S 15/931 |

FOREIGN PATENT DOCUMENTS

| CN | 107458555 A | * 12/2017 | ........... B63C 9/1255 |
| CN | 111341070 A | * 6/2020 | ............. G01D 21/02 |
| EP | 1961654 A1 | * 8/2008 | ............. A41D 7/003 |

* cited by examiner

*Primary Examiner* — Fekadeselassie Girma
(74) *Attorney, Agent, or Firm* — AlphaPatent Associates Ltd.; Daniel J. Swirsky

(57) ABSTRACT

An apparatus for detection of drowning conditions, the apparatus including three depth/pressure sensors attached to a user's torso for identifying angles of the torso in two axes in relation to the water level and two depth/pressure sensors for assessing respiration patterns.

11 Claims, 27 Drawing Sheets

SwimBIT system overview. Examples of acquired data, representing the swimmer's body pitch and roll, respectively (crosses represent the detected stops, circles represent the detected turns).

Table 1. Results obtained for body balance, body rotation, and trunk elevation.

| Athlete Sex | Style | | Body Balance (°) | Body Rotation (°) | Trunk Elevation (°) |
|---|---|---|---|---|---|
| Female | Butterfly | Min | −10.01 ± 6.87 | 6.17 ± 2.35 | 32.02 ± 7.86 |
| | | Max | −42.03 ± 3.91 | | |
| | Backstroke | Min | 6.43 ± 3.00 | 32.98 ± 9.37 | n.a. |
| | | Max | | −34.13 ± 3.44 | |
| | Breaststroke | Min | −9.17 ± 3.60 | 3.31 ± 4.97 | 31.44 ± 6.34 |
| | | Max | −40.60 ± 4.32 | | |
| | Front Crawl | Min | −18.81 ± 0.92 | 49.51 ± 9.67 | n.a. |
| | | Max | | −51.83 ± 9.48 | |
| Male | Butterfly | Min | 8.33 ± 9.21 | −2.00 ± 3.29 | 38.27 ± 8.81 |
| | | Max | −29.94 ± 8.61 | | |
| | Backstroke | Min | 0.01 ± 6.00 | 33.85 ± 15.62 | n.a. |
| | | Max | | −30.13 ± 6.76 | |
| | Breaststroke | Min | −3.59 ± 8.57 | −1.48 ± 3.72 | 26.15 ± 8.30 |
| | | Max | −29.74 ± 7.61 | | |
| | Front Crawl | Min | −7.69 ± 5.32 | 47.95 ± 10.23 | n.a. |
| | | Max | | −49.62 ± 9.74 | |

Maximum (Max) and minimum (Min) average values are presented in the dominant component of the motion in each style, while the mean value is presented in the nondominant component; n.a—not applicable.

FIG. 6B

| | D0' | D5' | 30A' | 30B' | 28' |
|---|---|---|---|---|---|
| 52A ⇒ | | | | | |
| 52B ⇒ | | | | | |
| 52C ⇒ | | | | | |
| 52D ⇒ | | | | | |
| 52E ⇒ | | | | | |
| 52F ⇒ | | | | | |

APPARATUS FOR DETECTION OF DROWNING CONDITIONS

CROSS-REFERENCE TO RELATED APPLICATIONS

This application claims the benefit of priority from U.S. Provisional Patent Application No. 63/133,801 filed Jan. 5, 2021, the disclosure of which is incorporated herein by reference.

TECHNICAL FIELD

The invention relates to the field of swimming accessories. More particularly, the invention relates to a method and apparatus for detection of drowning conditions.

BACKGROUND

Existing systems used to detect if a person swimming in the sea or in a pool is about to drown are not able to identify whether the person is with the nose and mouth inside the water, or if the person is not deep in the water, they are unable to make a direct measurement of head position without placing any sensor on the head.

Many patents and articles describe the detection of a drowning condition using systems which combine use of inertial motion sensors, respiration sensors, pulse sensors, etc. Some systems use a combination of a depth gauge (usually pressure gauge) attached to the upper part of the body combined with a timer capable of detecting extreme conditions such as swimming deep underwater for a long time.

Most, if not all, drowning detection systems are unable to distinguish between a state of a person drowning in a shallow depth and a state in which a person swims and the breathing is irregular and the pulse is accelerated (for example, a state in which the person swims with the mouth close to the water). The inability to distinguish between a drowning condition and a swimming condition such as that described above is due to the lack of knowledge of whether a person's mouth or nose is out of the water. There are inventions that contain a depth sensor above the neckline (such as placing the sensor on a swimming cap, or goggles, etc.). These solutions allow real-time knowledge of the position of the head relative to the surface of the water. The main disadvantage of this type of invention is the need to wear the product on the head while in the water. In this condition, the product may detach from the body and lose its effectiveness in detecting a drowning condition.

The object of the present invention is to provide a solution for the automatic detection of a drowning condition, including borderline states of swimming in depth in which the mouth and nose are close to the surface of the water and without sensors located on the head/neck.

SUMMARY

An apparatus for detecting drowning conditions, the apparatus including three depth/pressure sensors attached to a user's torso for identifying angles of the torso in two axes in relation to the water level and two depth/pressure sensors for assessing respiration patterns.

BRIEF DESCRIPTION OF THE DRAWINGS

FIGS. 6A and 6B depict a selected part of an article example of illustrating the ability to extract relevant data required for effective comparison against the data measured by the system.

DETAILED DESCRIPTION

An aspect of the present invention relates to a system for detecting a drowning condition including 3 or more pressure sensors to detect depth/location relative to the water level and to detect the upper body angular position relative to the water level. The sensors may include a piezoelectric pressure sensor, a capacitive pressure sensor, among others. In addition, the system may include one or more pressure sensors to detect respiration patterns. These sensors may include piezoelectric sensors, piezo-resistive sensors, and capacitive sensors, among others. The three pressure sensors may be located in the upper body with two of them located in the front of the body and one of them located in the back or the opposite.

Figure 1:
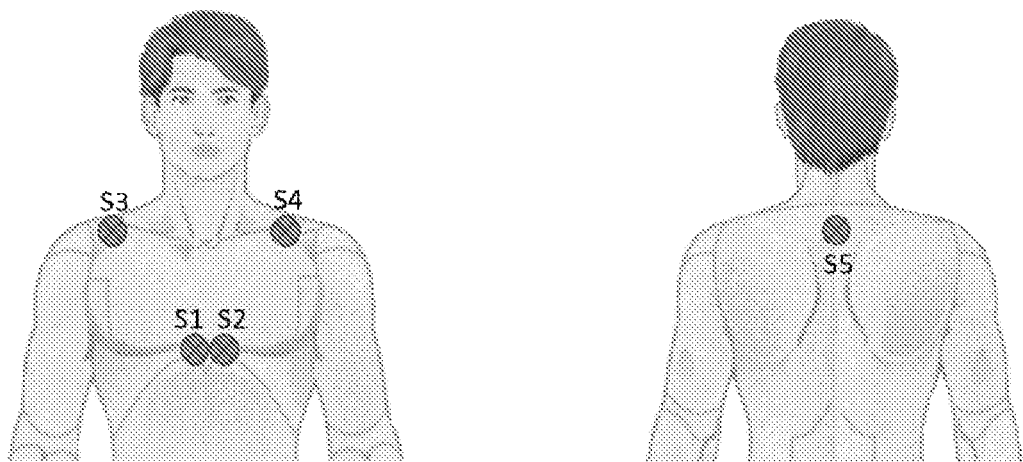
FIG. 1 depicts the location of the depth and respiration pattern sensors according to one embodiment of the invention.

FIG. 1 depicts the location of the depth and respiration pattern sensors according to one embodiment of the invention. Each pressure sensor may be used to measure and determine its depth (distance) relative to the water surface. The combination of the three distances of the pressure sensors from the surface defines a plane in the space where these three points are located. Calculating this plane makes it possible to know the angles of the upper body relative to the water surface and to estimate whether the mouth and nose are in the water.

Figure 2:
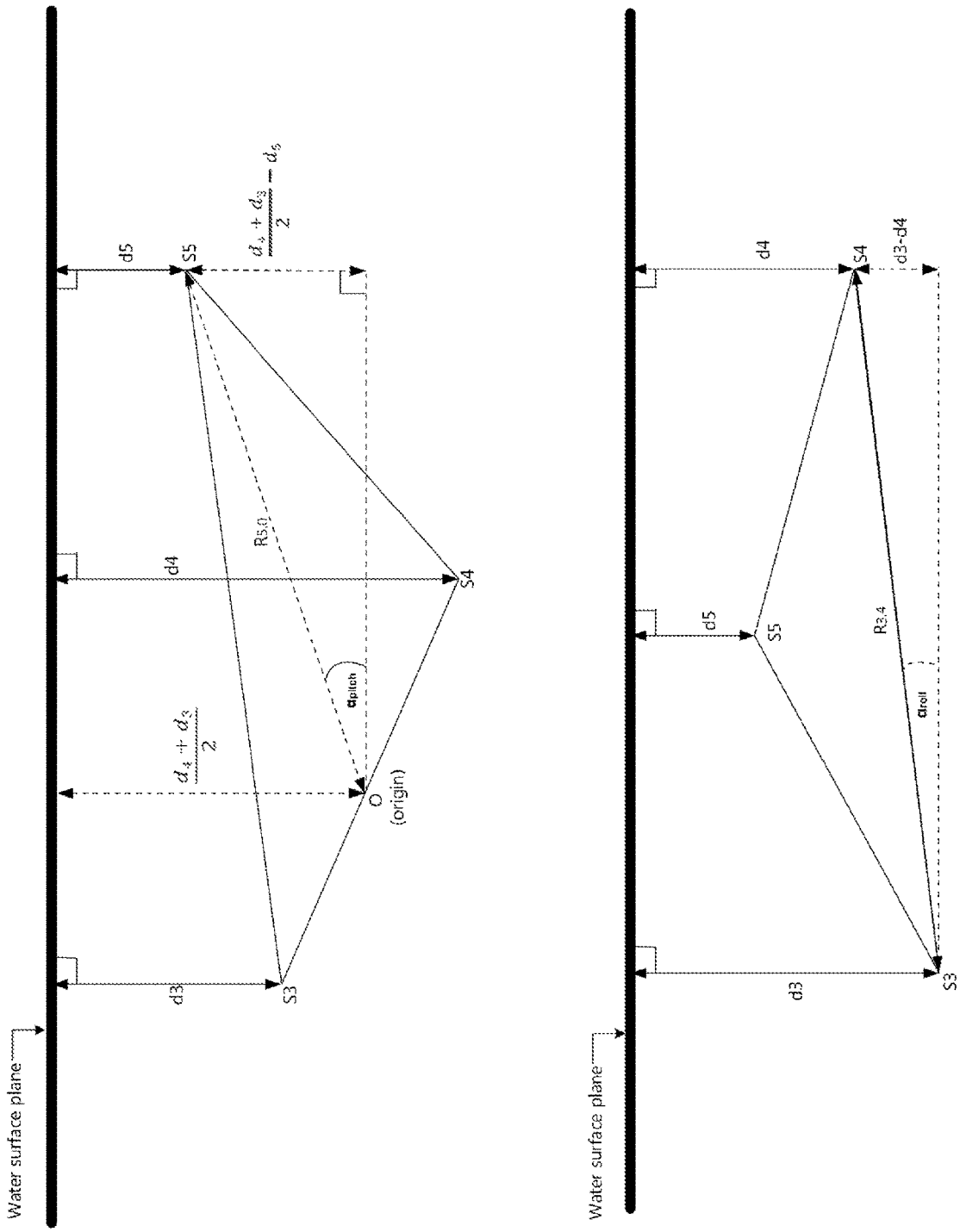
FIG. 2 depicts trigonometric relation between measured depths and pitch and roll angles of upper body relative to water surface plane.

FIG. 2 depicts trigonometric relation between measured depths and pitch and roll angles of upper body relative to water surface plane according to the trigonometric relations:

$$\alpha_{pitch} = \sin^{-1}\left(\frac{\frac{d_4+d_3}{2}-d_5}{R_{5,0}}\right)$$

$$\alpha_{roll} = \sin^{-1}\left(\frac{d_3-d_4}{R_{3,4}}\right)$$

The estimation of whether the mouth and nose are in the water is based on anatomical dimensions together with calculated torso's depth and angles (pitch and roll).

Figure 3:
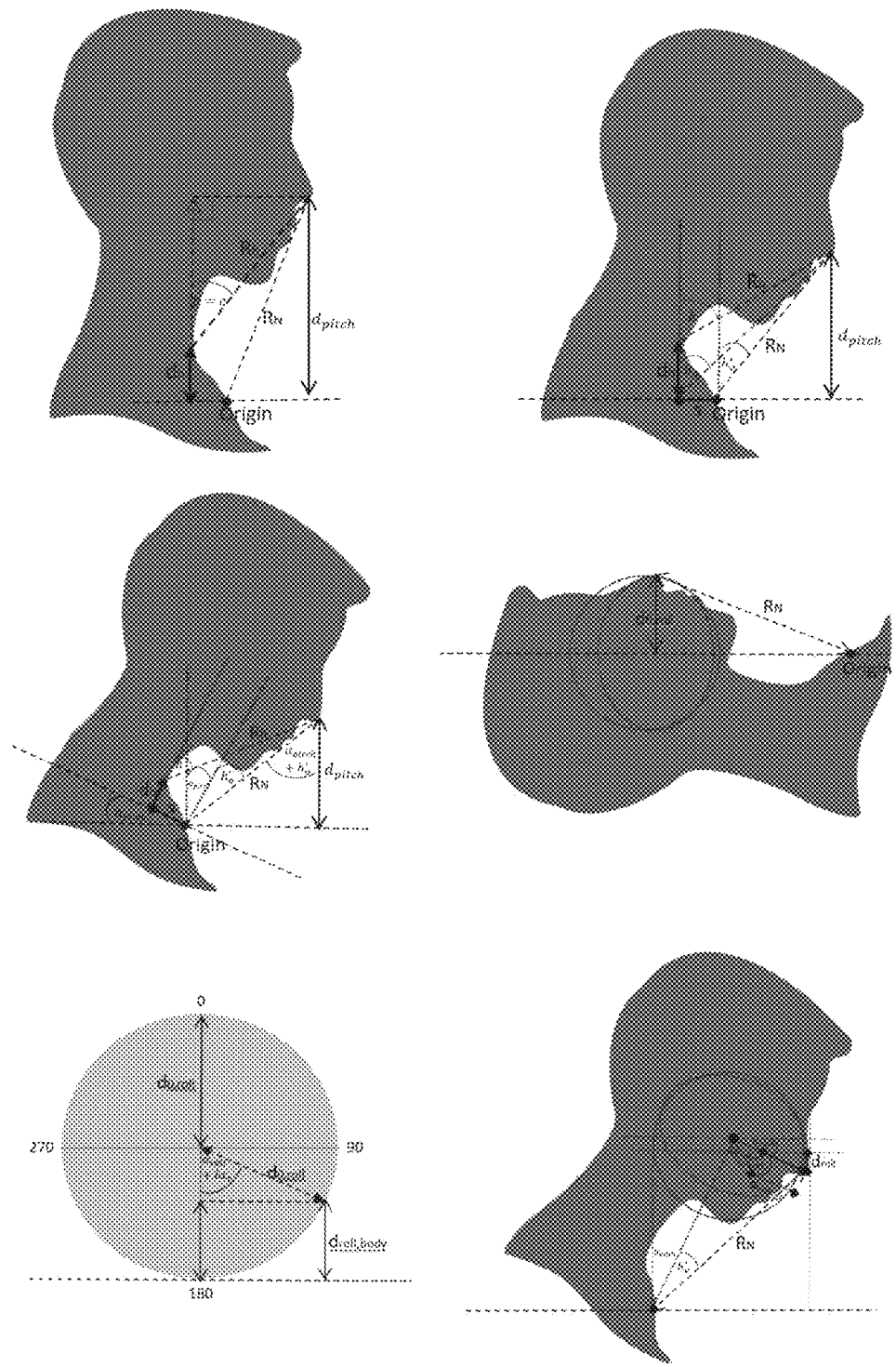
FIG. 3 depicts geometric dimensions and angles for drown depth calculations.

FIG. 3. depicts relative distances between the mouth/nose and the three sensors ($R_h$, $d_h$, s, c) according to the trigonometric calculations:

$$d_{drown\_depth} = d_{pitch} + d_{roll}$$

$$d_{pitch} = R_N \cdot \cos(\alpha_{pitch} + h_o')$$

$$d_{roll} = d_{roll,body} \cdot \sin(\alpha_{pitch})$$

where:
$R_h$—constant distance between head tilt axis point (on neck) and nose
$d_h$—constant distance between head tilt axis point and origin plane (horizontal)
s—constant distance between head tilt axis point and origin point
c—constant angle between nose and vertical at head tilt axis point
$ht_p$—input angle of front or back (pitch) head tilt
$ht_r$—input angle of side (roll) head tilt
$h_o$—front/back head tilt angle shifted to origin plane
$h_o'$—front/back head tilt angle shifted to origin point
$R_N$—distance between nose and origin $$h = c + ht_p$$

$$\tan(h_o) = \frac{R_h \cdot \sin(h)}{R_h \cdot \cos(h) + d_h}$$

$$\tan(h_o') = \frac{R_h \cdot \sin(h) - s}{R_h \cdot \cos(h) + d_h}$$

$$R_N = \frac{R_h \cdot \cos(h) + d_h}{\cos(h_o')}$$

$$d_{0,roll} = R_N \cdot \sin(h_o')$$

$$d_{roll,body} = d_{0,roll} \cdot (1 - \cos(\alpha_{roll} + ht_r))$$

These distances vary between people of different height, sex, race, age, etc. The standard deviation of this variable can be significantly decreased by using relevant anthropometry statistical data tailored by the overall height of the individual—a measure closely correlated to the size of the swim-suite fitted with wearable pressure sensors.

Figure 4:
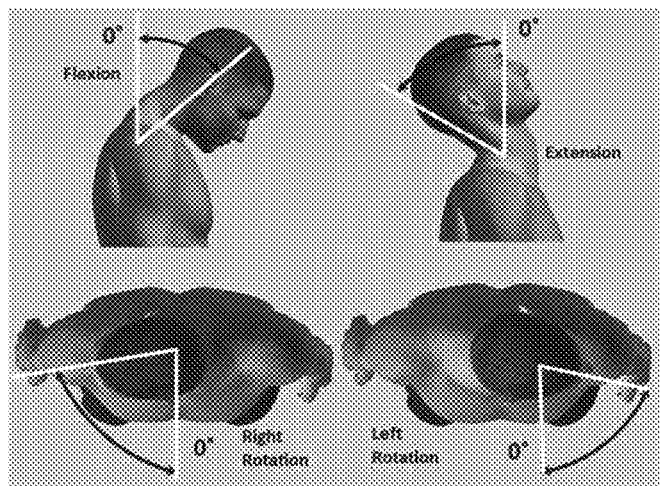
FIG. 4 depicts different head tilt positions limits used for depth calculations.

FIG. 4 depicts examples of the neck joint angles relative to the torso. Assuming the person is tilting his\her head towards the water surface can increase the maximal breathing depth. The head tilt added value for the ability to reach the surface with the mouth/nose will be simplified to constants representing near maximal flexion/extension and/or side rotation of the head.

To determine whether the given body's submersion state has the ability to breath, we should compare the maximal depth of breathing at the current calculated a angles (pitch and roll) to the measured depth of the origin point.

If the origin's measured depth is greater (deeper) than the maximal depth of breathing, then a submerged indication will arise for the current time-frame.

By measuring the time duration in which the mouth and nose are inside the water, the potential of a drowning condition may be determined. A drowning condition may be determined based on a time measurement where the nose and mouth are in the water for a cumulative time period of 40 seconds or other predetermined amount of time during the last minute, or over another continuous period of time.

The measurements by these 3 depth/pressure sensors allow the system to compare the measured body movements to known swimming styles patterns (such as front crawl, backstroke, breaststroke, butterfly, sidestroke etc.). All these common swimming styles are expressed in cyclical movements of the torso.

These movements are expressed by unique pitch and/or roll angles of the torso. Extensive academic studies have been carried out to map the statistics of the different swimming styles for performance improvement. These studies have created databases that incorporate parameters required for real-time comparison to identify swimming patterns. Therefore, if the measured body angles match with these statistical databases, then the system would conclude that the person is swimming and there is no need for floatation process activation.

Figure 6A:
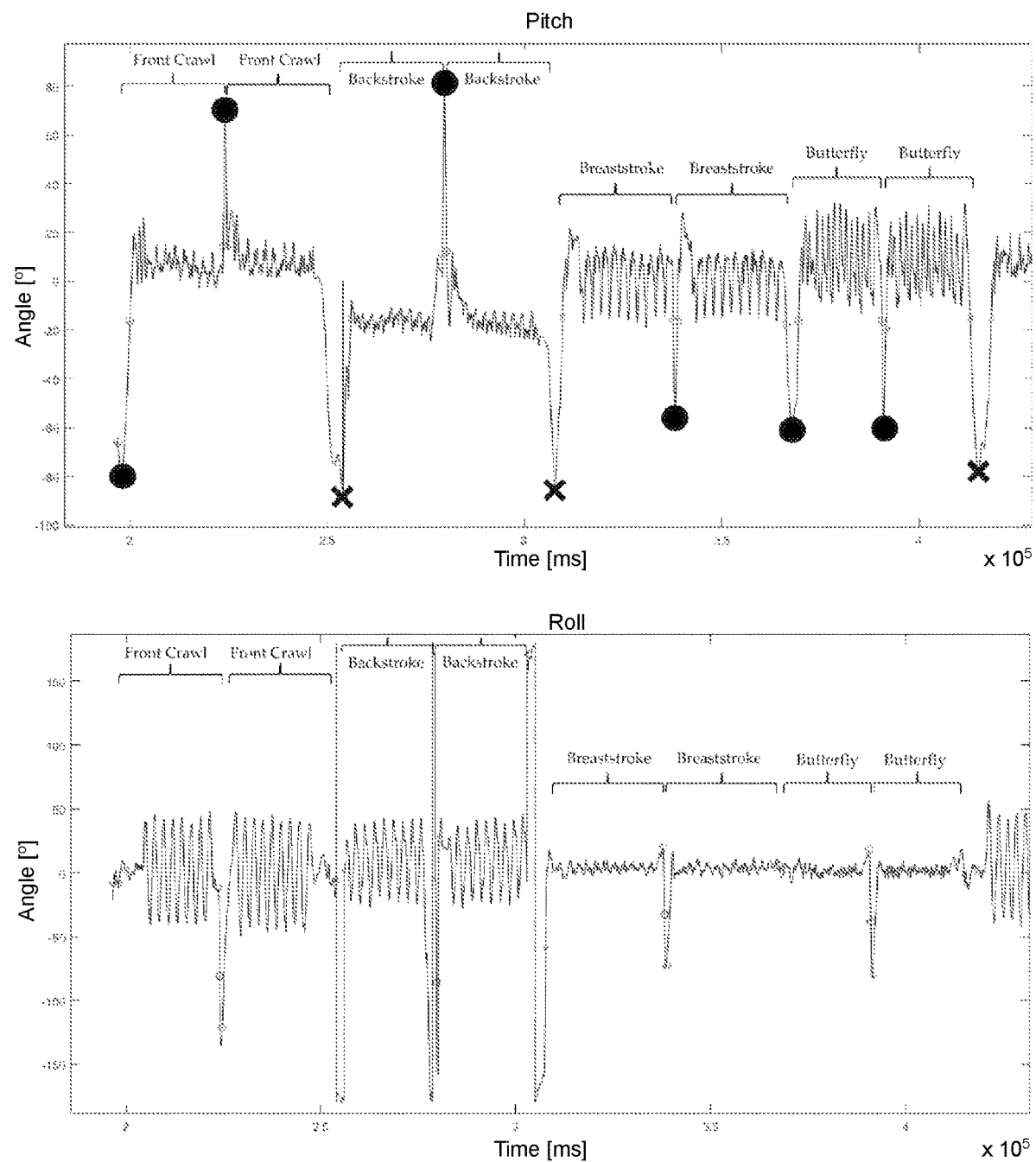

FIGS. 6A and 6B depict an article example from "SwimBIT: A Novel Approach to Stroke Analysis during swim training based on Attitude and Heading Reference System (AHRS". The example illustrates the ability to extract relevant data required for effective comparison against the data measured by the sensors.

In some embodiments, the system may include 2 pressure sensors located on the chest and/or in the area of the diaphragm whose function is to detect abnormal respiration patterns. The two sensors may be located close to each other. One of the sensors may be positioned between the user's chest and an elastic band which secures the sensor to the chest. This sensor is oriented so it can measure the total pressure based on the hydrostatic and hydrodynamic pressure inside the water and the pressure exerted by the expansion of the chest against the elastic belt. The second sensor may be positioned between the user's chest and the elastic band oriented at an angle relative to the first sensor and measure only hydrostatic and hydrodynamic pressure (does not measure pressure associated with chest expansion). Alternatively, the second sensor may be positioned on the outer side of the elastic band and measure only hydrostatic and hydrodynamic pressure (does not measure pressure associated with chest expansion). Alternatively, one of the three sensors S3,S4,S5 may be used as the second sensor for respiration abnormality detection. In this case due to the distance between the sensors, pressure compensation may be needed.

In some embodiments, a controller may process the pressure information received from both sensors and may determine the pressure due to the chest expansion by cancelling out the hydrostatic and hydrodynamic pressure measurements of both sensors:

$$S1_{pressure} = S1_{hydrostatic\&hydrodynamic} + S1_{breathing}$$

$$S2_{pressure} = S2_{hydrostatic\&hydrodynamic}$$

In the case that S1 is locate near S2, we can assume that the hydrostatic and hydrodynamic water pressure is the approximately the same for both of the sensors:

$$S1_{hydrostatic\&hydrodynamic} \approx S2_{hydrostatic\&hydrodynamic}$$

From the equations above, we can conclude that:

$$S1_{breathing} = S1_{pressure} - S2_{pressure}$$

In the case that S1 is not locate near S2, we can first compensate the distance difference between the sensors and then cancel out the hydrostatic and hydrodynamic pressure.

Alternatively, the system can use one strain-gauge embedded within an elastic band, instead of the two pressure sensors described above (S1,S2).

Based on the resulting measurement of chest expansion pressure, the controller may determine the respiration pattern of the user.

Figure 5:
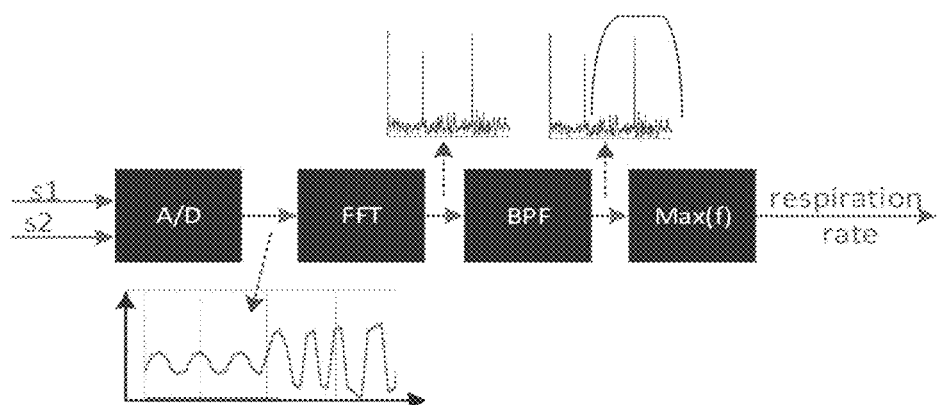
FIG. 5 depicts one embodiment of respiration rate/pattern estimation using respiration pattern sensors.

FIG. 5 depicts one example of performing computations of the respiration pattern. The controller may use estimation methods such as FFT or other methods of spectral analysis. Noise may be filtered out and the maximum respiration frequency and amplitude may be determined.

Conclusions regarding respiratory pattern regularity can be achieved using these measured parameters (frequency and amplitude of respiration) by comparing the measurements to predetermined thresholds of normal respiration. Mostly, in drowning conditions, we can find that the body is entering and exiting the water in an attempt to breathe, so we can find increase in the respiration rate. Further distress would usually result in water swallowing causing rapid convulsions and spasm—which also increase the appeared respiratory movement frequency. Normal respiration rate is between 10-40 breathing per minute. A distress situation (like drowning) will increase that rate to above 40 breathing per min.

The decision-making algorithm may then use one or more of the following parameters previously calculated to determine whether a drowning condition is taking place:
 a. The duration of time the nose and mouth are immersed in water (continuous time or a fragmented period of time within a defined moving time frame)
 b. The assessment whether a person's movements resemble any of known swimming styles' patterns. If a resemblance is detected, then the assessed drowning risk may be decreased.
 c. Respiratory regularity based on the frequency and amplitude of the chest/diaphragm movement. Based on the result, the system may provide for automatic real-time detection of a drowning condition and may further provide for activation of a rescue mechanism, for example, by opening a valve in a gas container to inflate a flotation device. The floatation device may be an existing product.

Figure 7:
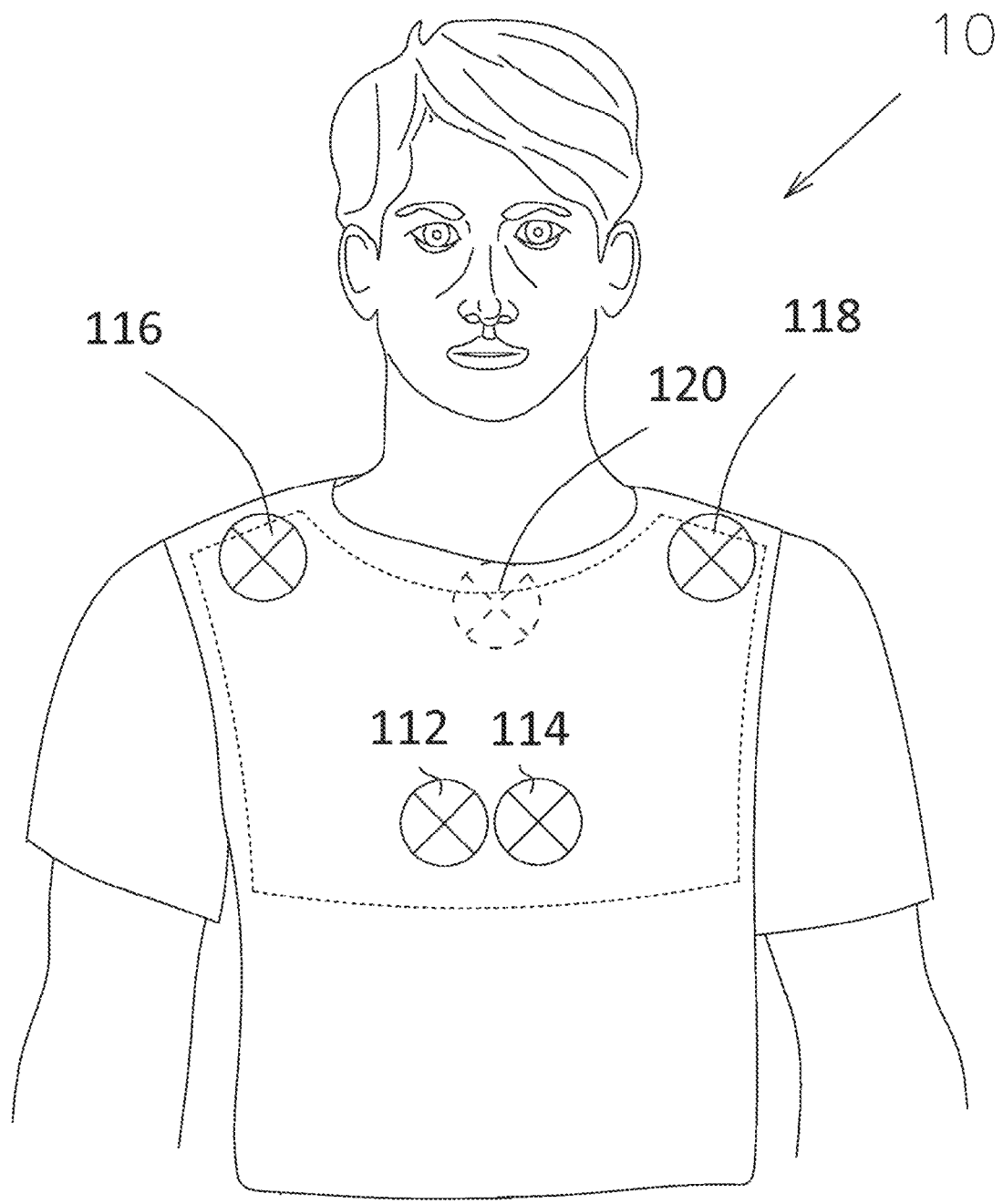
FIGS. 7,8,9,10,11 illustrate the drowning detection system.

FIG. 7 schematically illustrates a drowning detection system, according to an embodiment of the present invention. Shown in the figure is a front view of a person wearing a drowning condition detection shirt in a deflated mode (10). The shirt includes several sensors on the front (112, 114, 116, and 118) and one sensor on the back (120), being physical sensors or combined from physical sensors.

Figure 8:
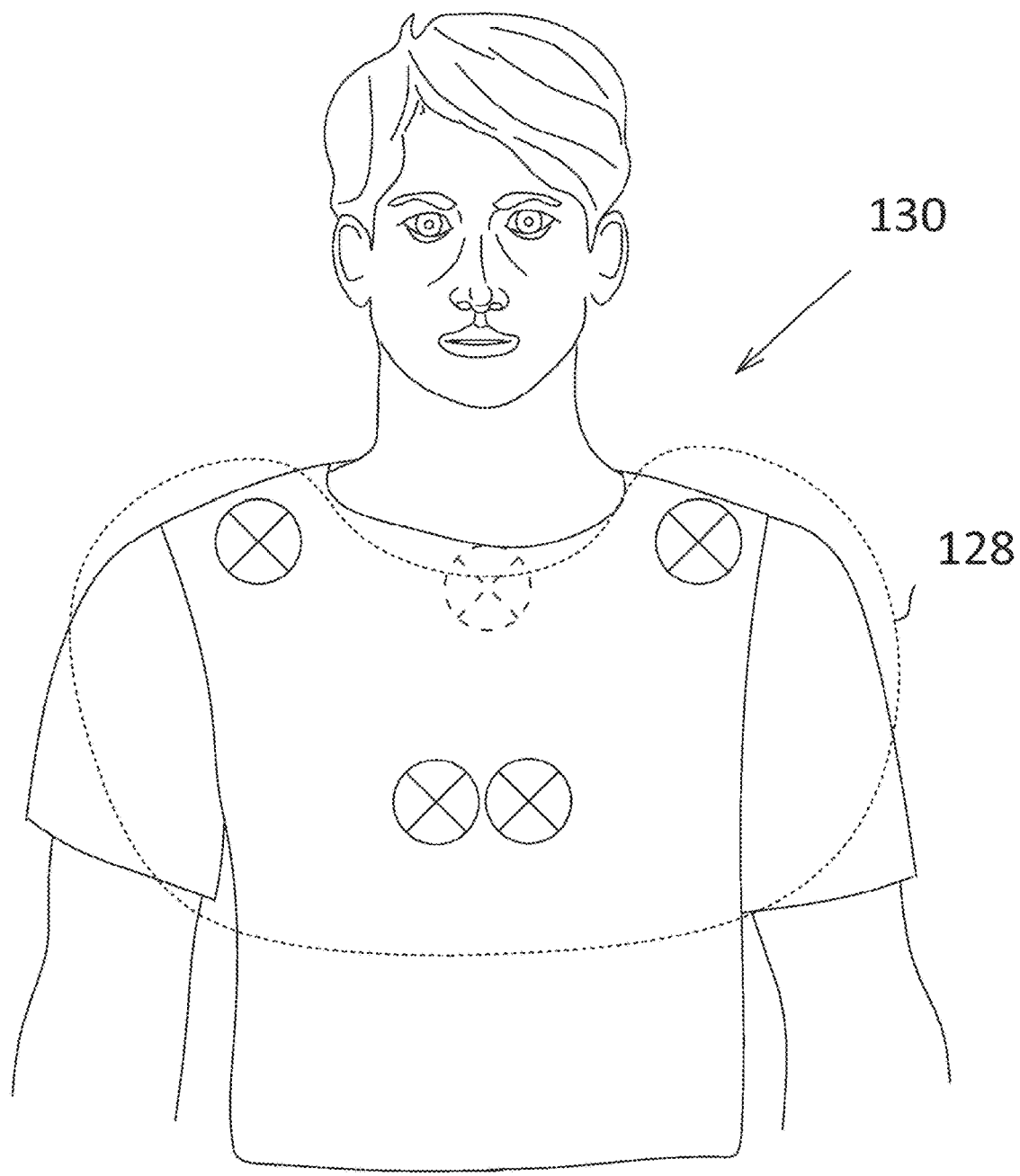

FIG. 8 schematically illustrates the drowning detection system, according to an embodiment of the present invention. Shown in the figure is a front view of a person wearing the drowning condition detection shirt in an inflated mode (130). In this mode, inflator chamber (128) is filled with air after the system has detected a drowning condition.

Figure 9:
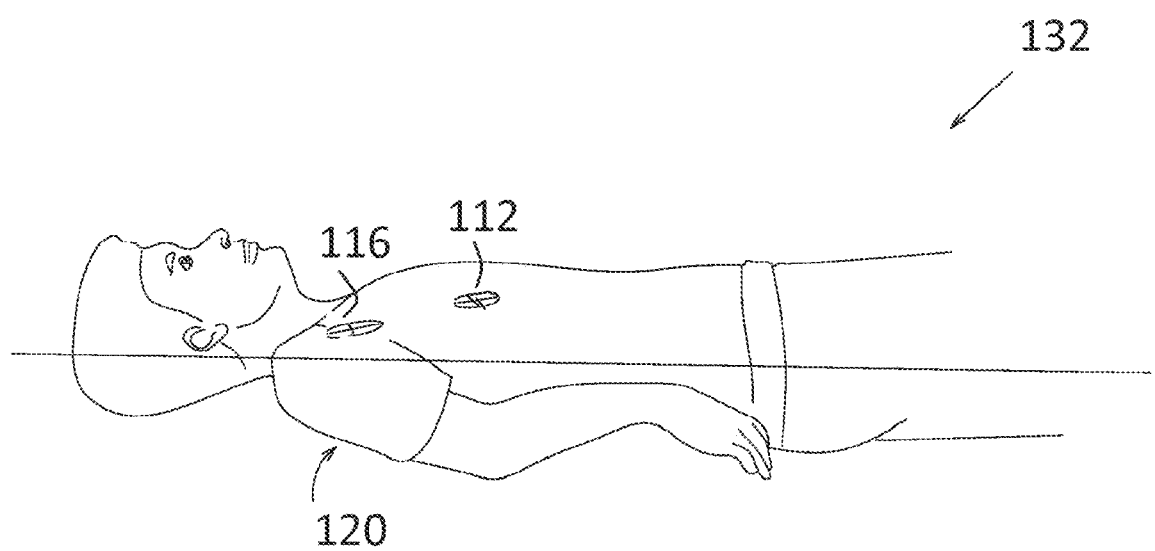

FIG. 9 schematically illustrates the drowning detection system, according to an embodiment of the present invention. Shown in the figure is a side view of a person floating in water (132). The system detects that it is not a drowning condition and the inflator chamber is not filled with air. Sensors (116, 118, and 120) detect the position and depth of the upper body (Lying on the back position) and the system determines that the mouth and nose are not immersed in water and therefore it is not a drowning condition, and does not activate inflation of the inflator chamber.

Figure 10:
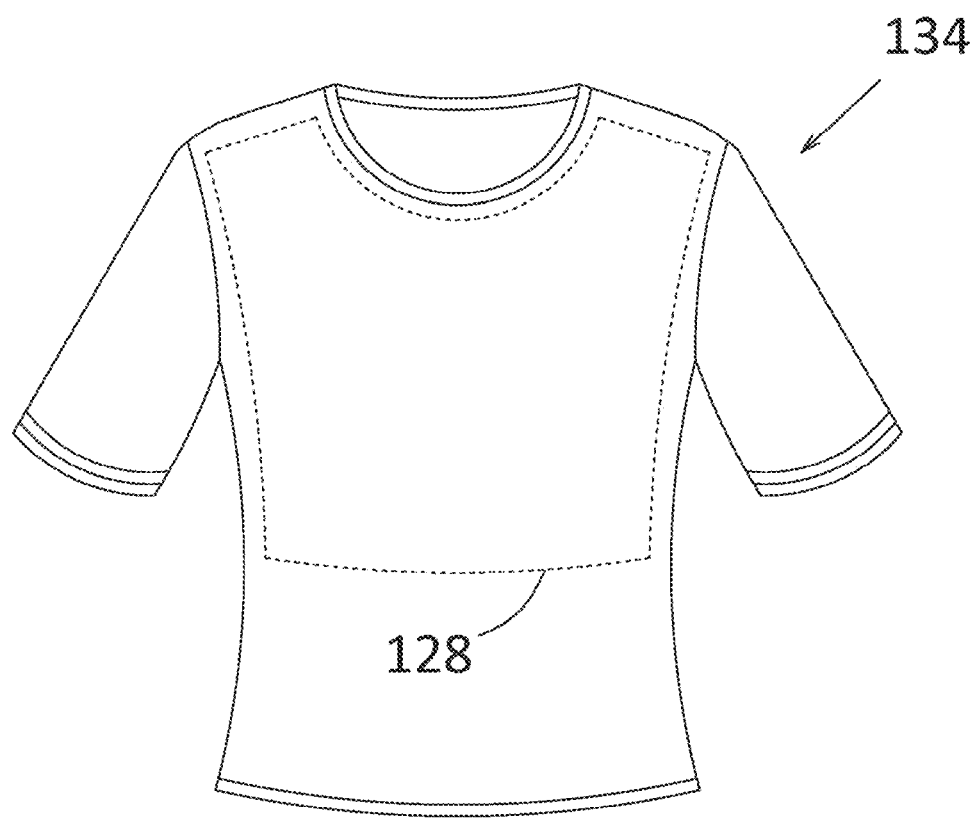
Figure 11:
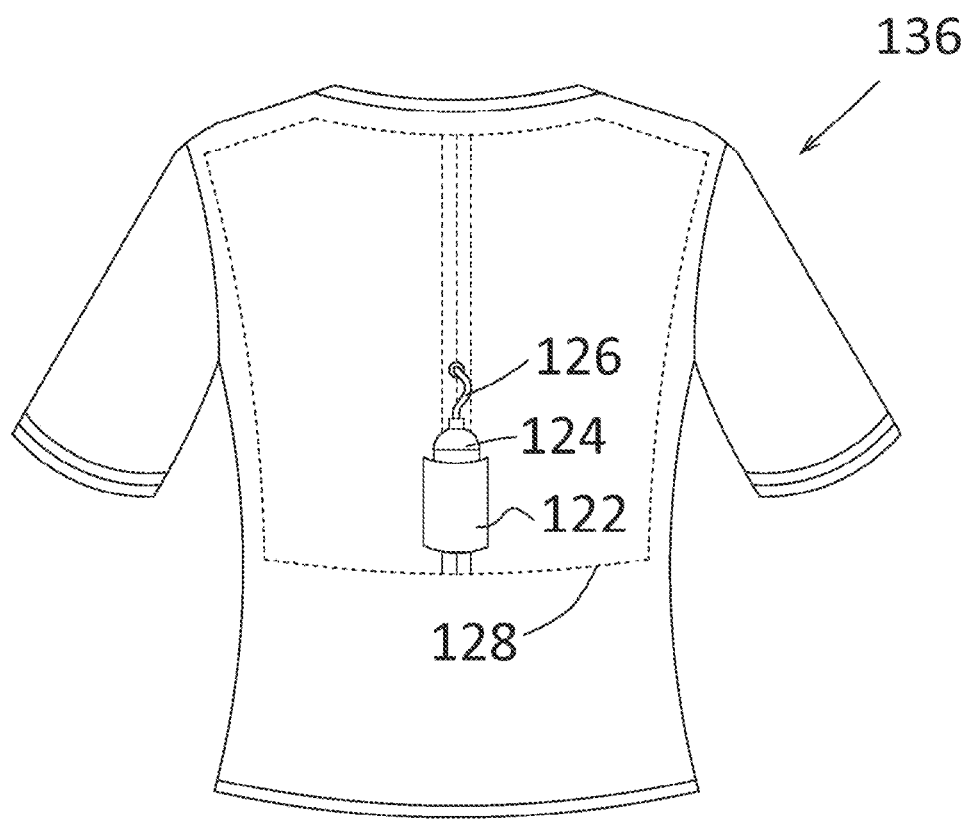
Figure 12:
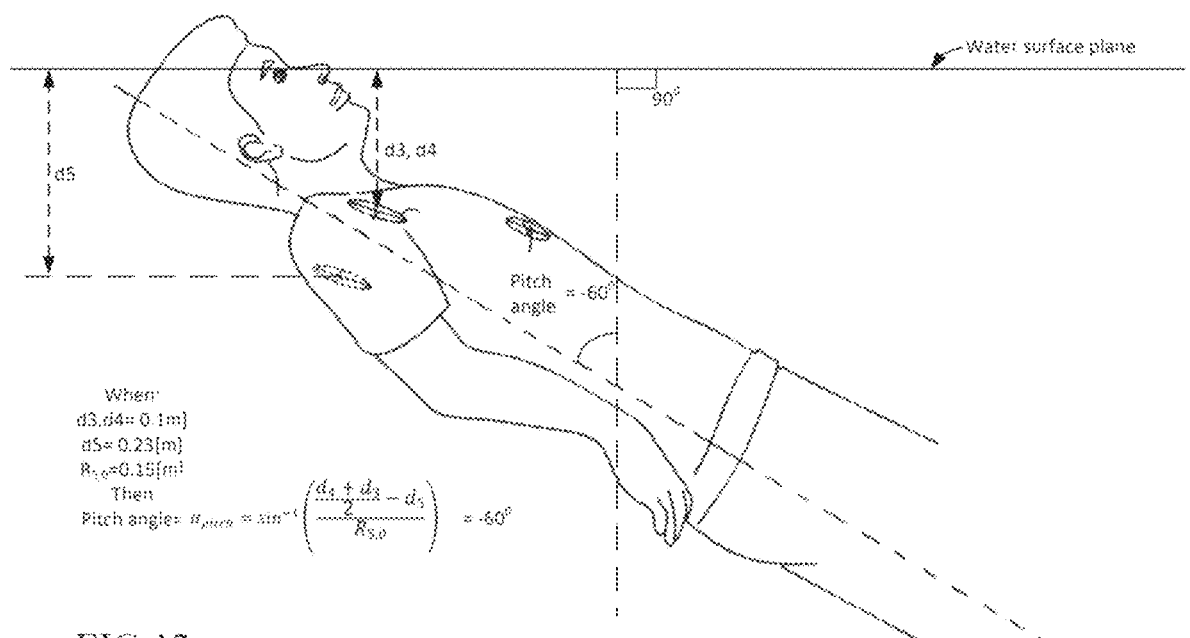
FIG. 12 is a side view of the user wearing the apparatus of FIG. 19, at a (−60) degrees pitch angle.
Figure 13:
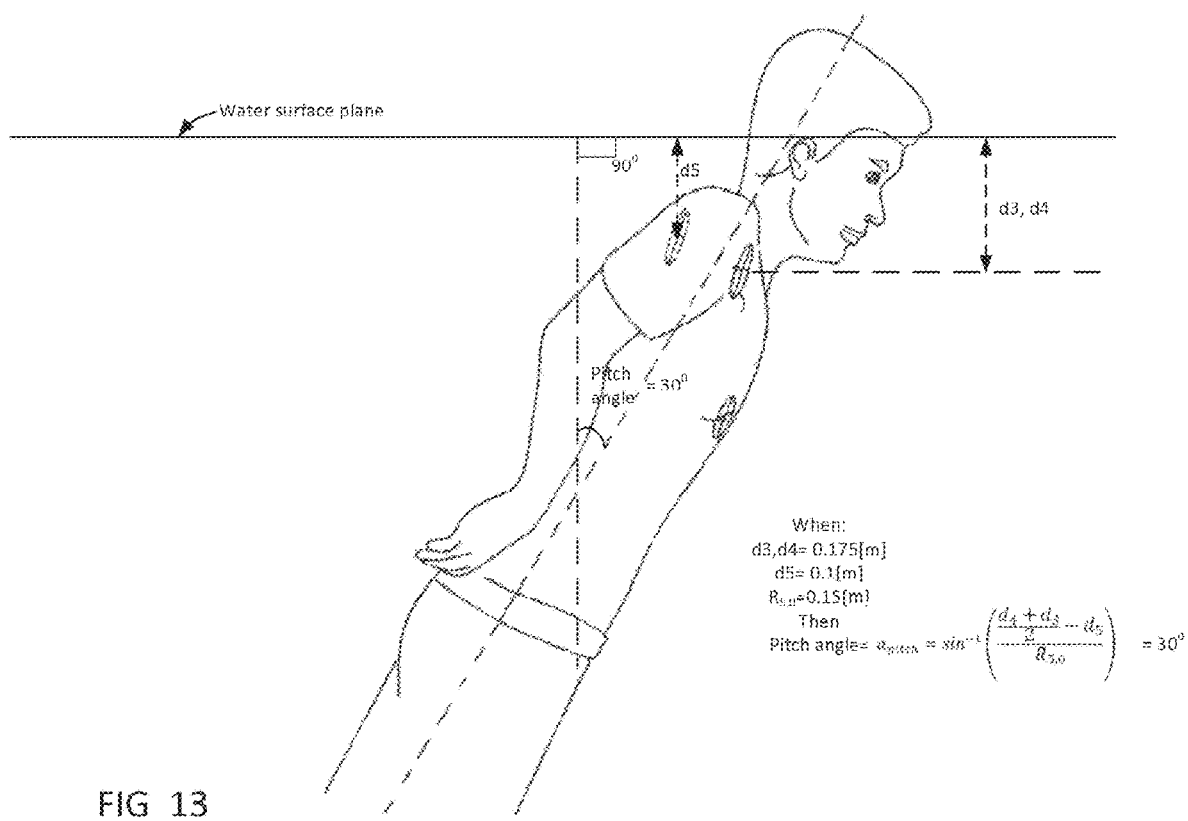
FIG. 13 is a side view of the user wearing the apparatus of FIG. 19, at a (30) degrees pitch angle.
Figure 14:
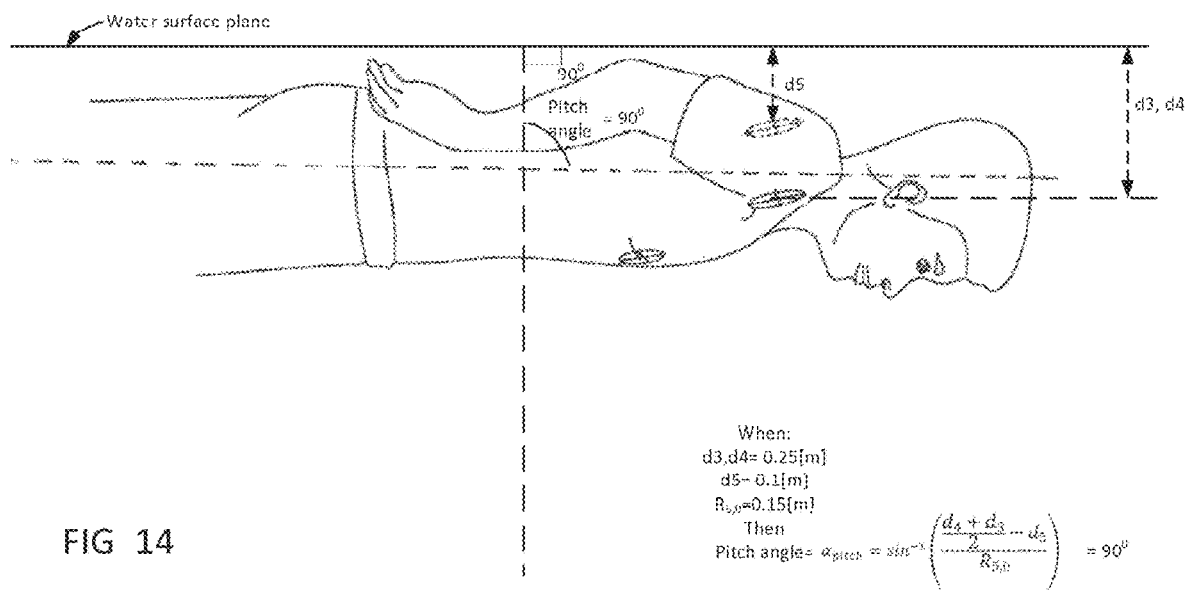
FIG. 14 is a side view of the user wearing the apparatus of FIG. 19, at a (90) degrees pitch angle.
Figure 15:
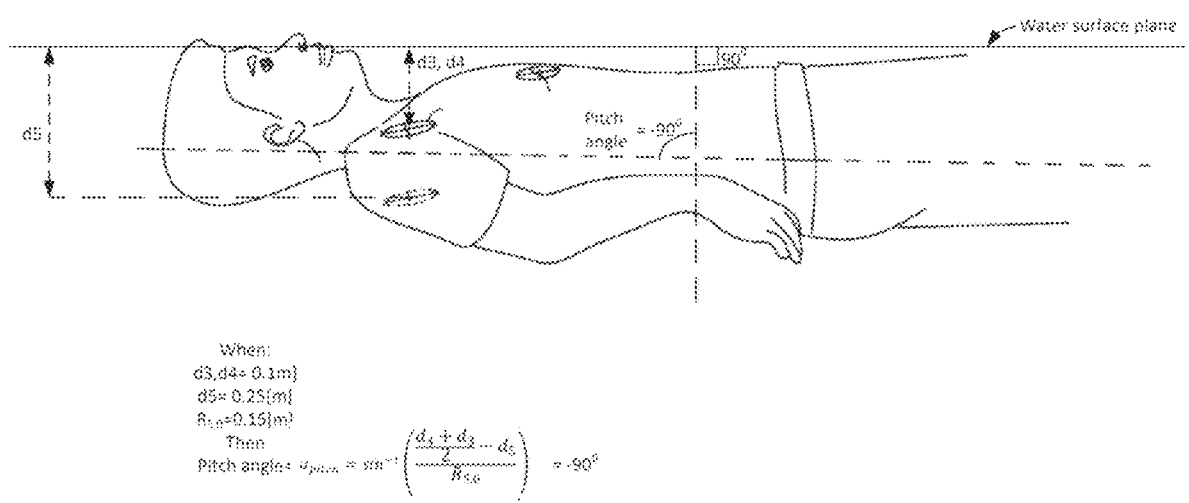
FIG. 15 is a side view of the user wearing the apparatus of FIG. 19, at a (−90) degrees pitch angle.
Figure 16:
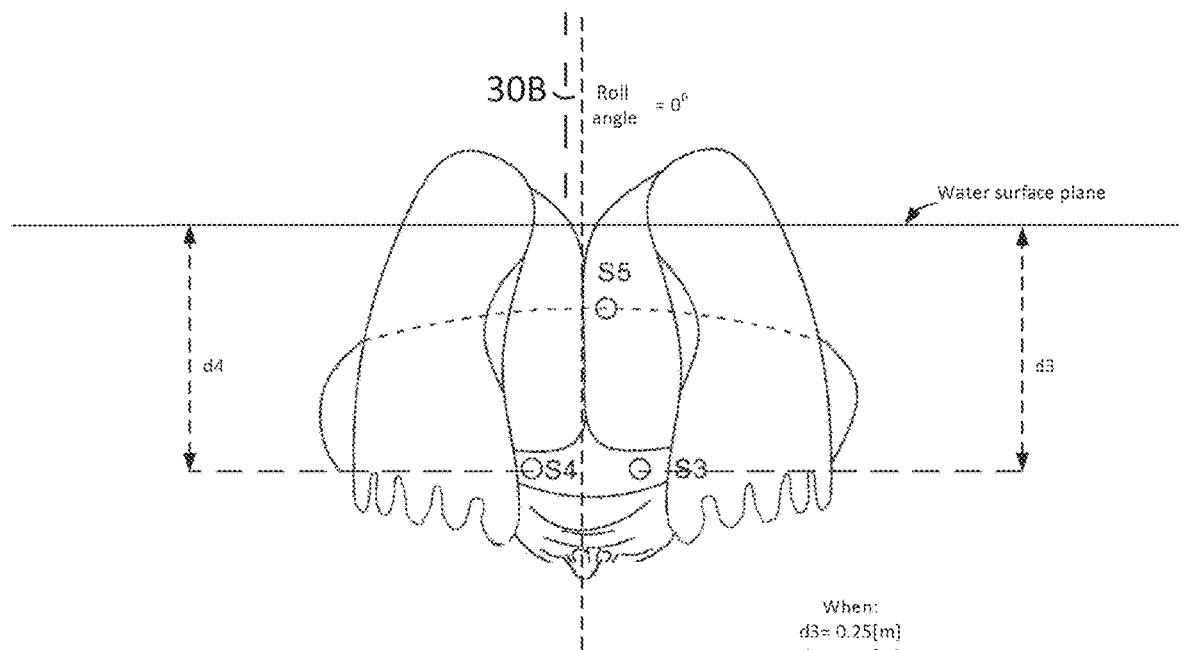
FIG. 16 is a rear view of the user wearing the apparatus of FIG. 19, at the (90) degrees pitch angle of FIG. 14, and of zero degrees roll.
Figure 17:
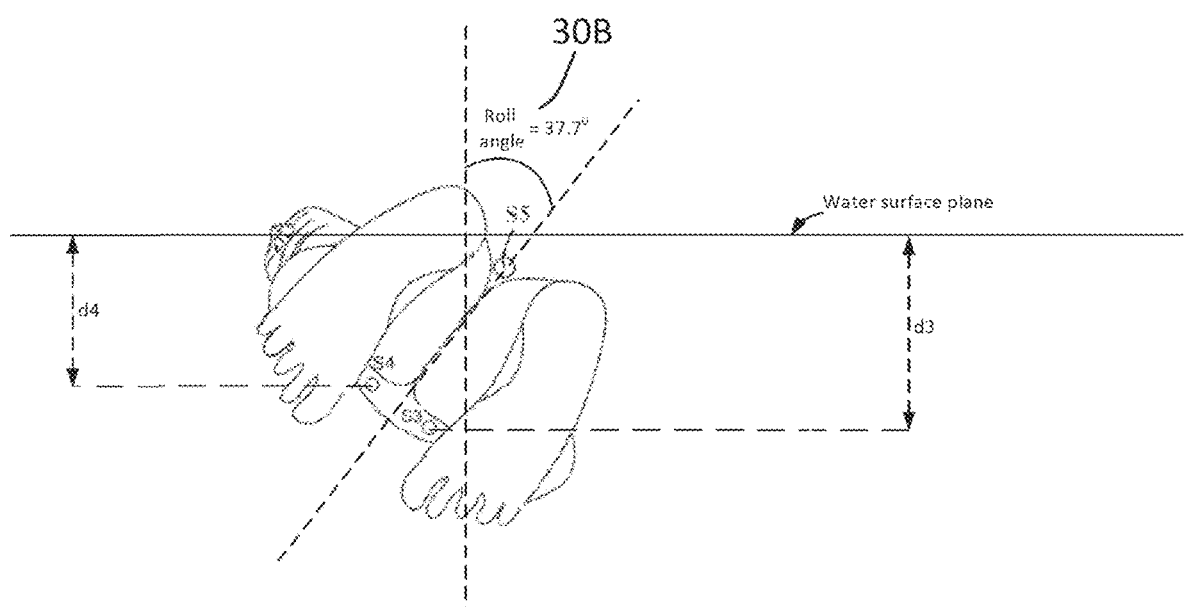
FIG. 17 is a rear view of the user wearing the apparatus of FIG. 19, at the (90) degrees pitch angle of FIG. 14, and of 37.7 degrees roll.
Figure 18:
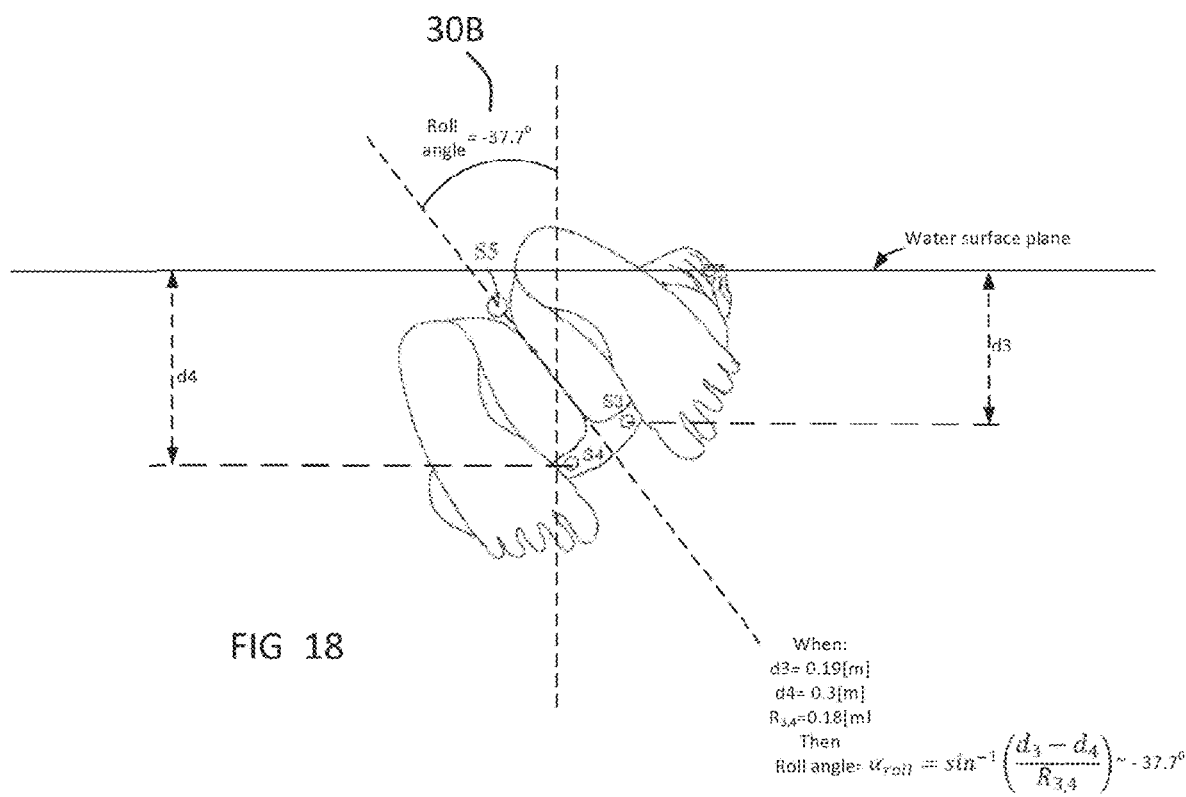
FIG. 18 is a rear view of the user wearing the apparatus of FIG. 19, at the (90) degrees pitch angle of FIG. 14, and of (−37.7) degrees roll.

FIGS. 10 and 11 schematically illustrates the drowning detection system, according to an embodiment of the present invention. Shown in the figure is a back view of the shirt (136) including the inflation chamber (128). The shirt includes a pocket (122) on the back of the shirt which holds a pressurized air tank (124) that is connected by means of a hose (126) to the inflator chamber (128).

FIGS. 12,13,14,15,16,17,18 illustrate the examples of different depth and angles of user's torso and the way the measurements of the depth/pressure sensors enable the calculation of pitch and roll angles for each body position as described above.

Figure 19:
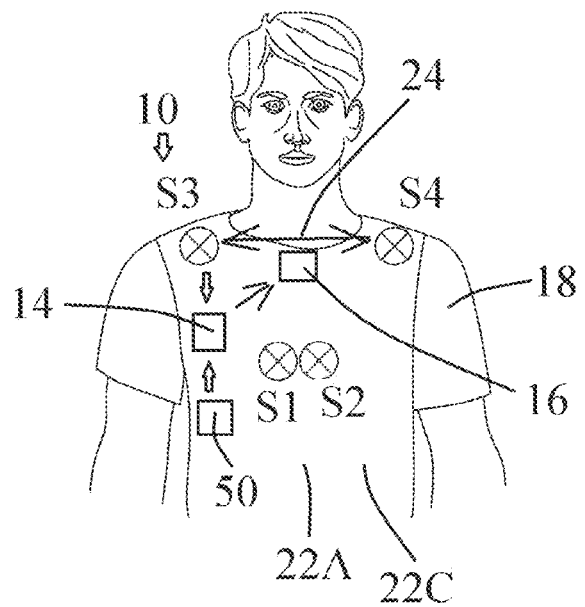
FIG. 19 is front view of a user wearing an apparatus.

FIG. 19 is front view of a user wearing an apparatus for detecting drowning according to one embodiment of the invention.

An apparatus 10 for alerting and avoiding drowning includes according to one embodiment of the invention, sensors such as S3 and others, which may be attached to a shirt 18 worn by the user; a controller 14, for calculating depth, angle of the user and additional parameters according to the sensors' measurements, and for determining risk of drowning accordingly; and a device 16 for being operated in case of the determined risk, such as to alert and/or to lift the user.

Figure 20:
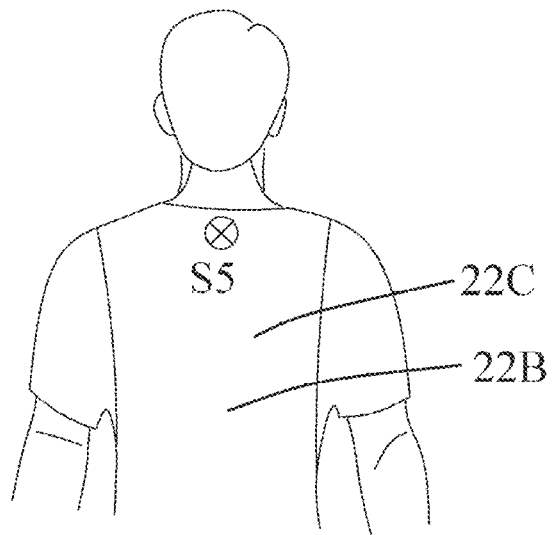
FIG. 20 is rear view of the user wearing the apparatus of FIG. 19.

FIG. 20 is rear view of the user wearing the apparatus of FIG. 19. Apparatus 10 may include a depth sensor S5 disposed at the top of the center of the back 22B of the user.

Figure 21:
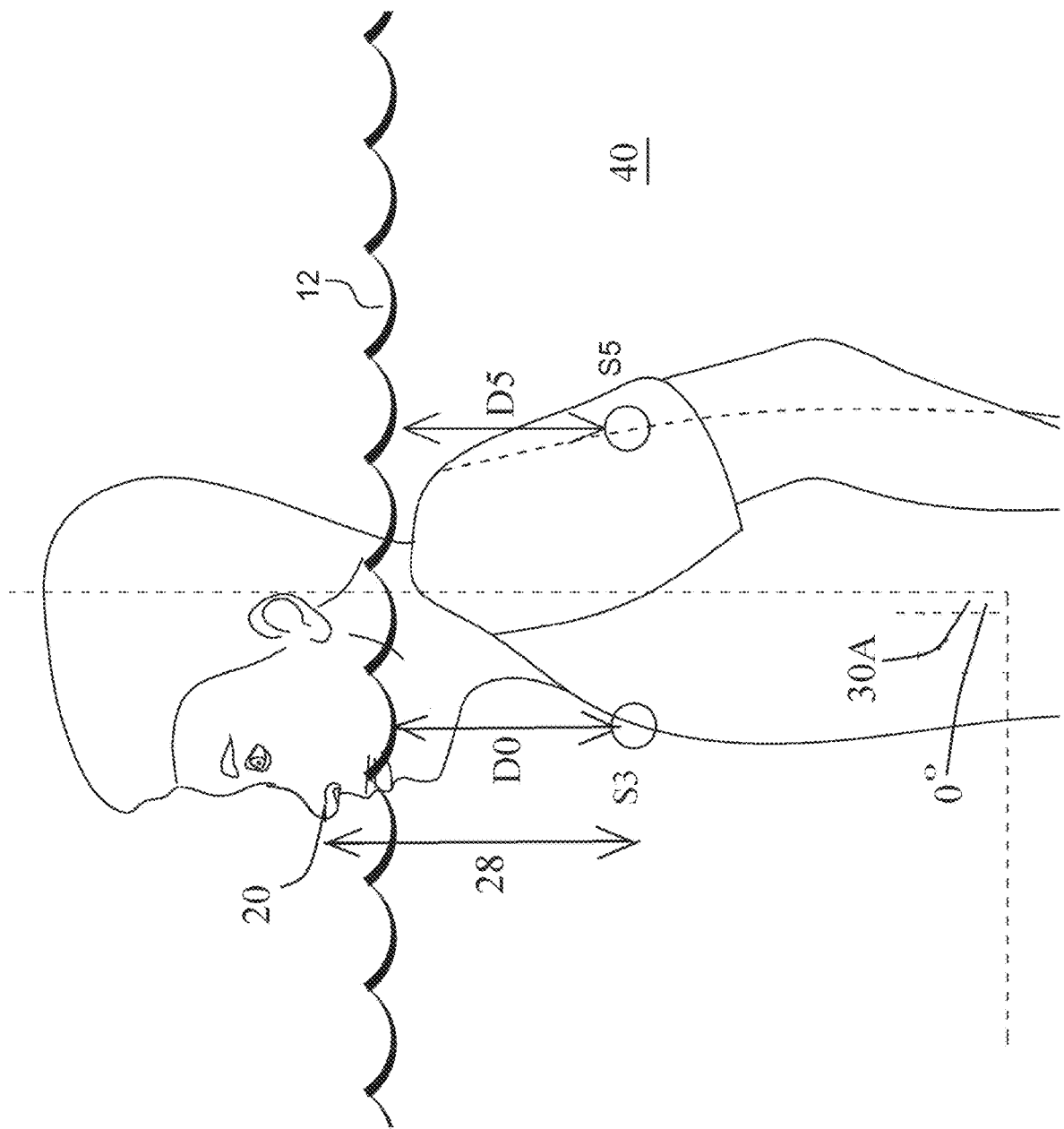
FIG. 21 is a side view of the user wearing the apparatus of FIG. 19, at a zero pitch angle.

FIG. 21 is a side view of the user wearing the apparatus of FIG. 19, at a zero pitch angle.

Controller 14 (FIG. 19) determines no risk of drowning in case the nose 20 of the user will be calculated to be disposed above the water level 12.

Referring again to FIG. 19, apparatus 10 may include depth sensors S3 and S4 disposed at the top of the front 22A of the torso 22C of the user, and being distanced (24) from one another.

Depth sensors S3, S4, and S5 are sufficient for perfectly determining depth and angles of torso 22C, since three location sensors are geometrically sufficient to determine any plane in the space.

Accordingly, sensors S3, S4, and S5 may approximately determine whether nose 20 is disposed above water level 12.

Figures 22, 23:
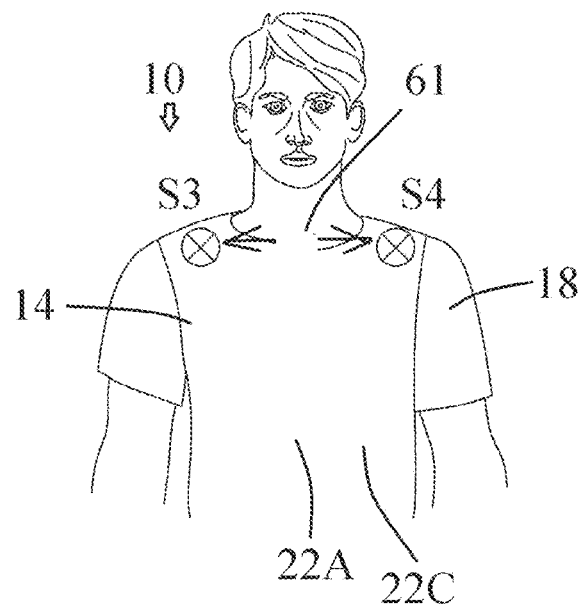
FIG. 22 is a front view depicting sensors used for angular positions' calculations.
FIG. 23 depicts some of the content of memory 50 of FIG. 19.

FIG. 22 is a front view depicting sensors used for angular positions' calculations.

A virtual depth sensor may be obtained from the measurements of sensors S3 and S4 of FIG. 19 for measuring the depth at the center 61 of the top of front 22A of torso 22C.

Apparatus 10 may include a pitch sensor and a roll sensor, for measuring pitch and roll of the user.

The virtual roll sensor may be obtained from the measurements of sensors S3 and S4 of FIG. 19 or by other sensor.

The virtual pitch sensor may be obtained from the measurements of the virtual depth sensor (61) combined with measurement of S5, or by measurements of sensors S3 combined with measurement of S5, or by measurements of sensors S4 combined with measurement of S5 or by sensors S3 and S4 and S5 of FIG. 19 or by another sensor.

A first approximation for detecting drowning may be obtained by measuring depth and pitch measurements only.

Referring again to FIG. 21, the zero angle pitch 30A may be determined in case depth D0 measured by the virtual depth sensor or by depth sensor S3 (or S4) is equal to D5 measured by depth sensor S5.

In this zero angle pitch case, controller 14 (FIG. 19) determines nose 20 is disposed above water level 12 in case the depth D0 is smaller than the distance 28 between by the virtual depth sensor or by depth sensor S3 and nose 20.

FIG. 23 depicts some of the content of memory 50 of FIG. 19.

Memory 50 includes groups of depths D0' for by the virtual depth sensor or by depth sensor S3 or S4, depths D5' for depth sensor S5, and pitches 30A' for which the nose is disposed above water level 12, and the measurements are compared to the groups of memory 50, which if found determines no risk of drowning.

Thus, a first group 52A compared for the measurements of FIG. 21 is of zero angle pitch, nose 20 is disposed above water level 12 in case the depth D0' is smaller than the distance 28 between by the virtual depth sensor or by depth sensor S3 or S4 and nose 20.

Figure 24:
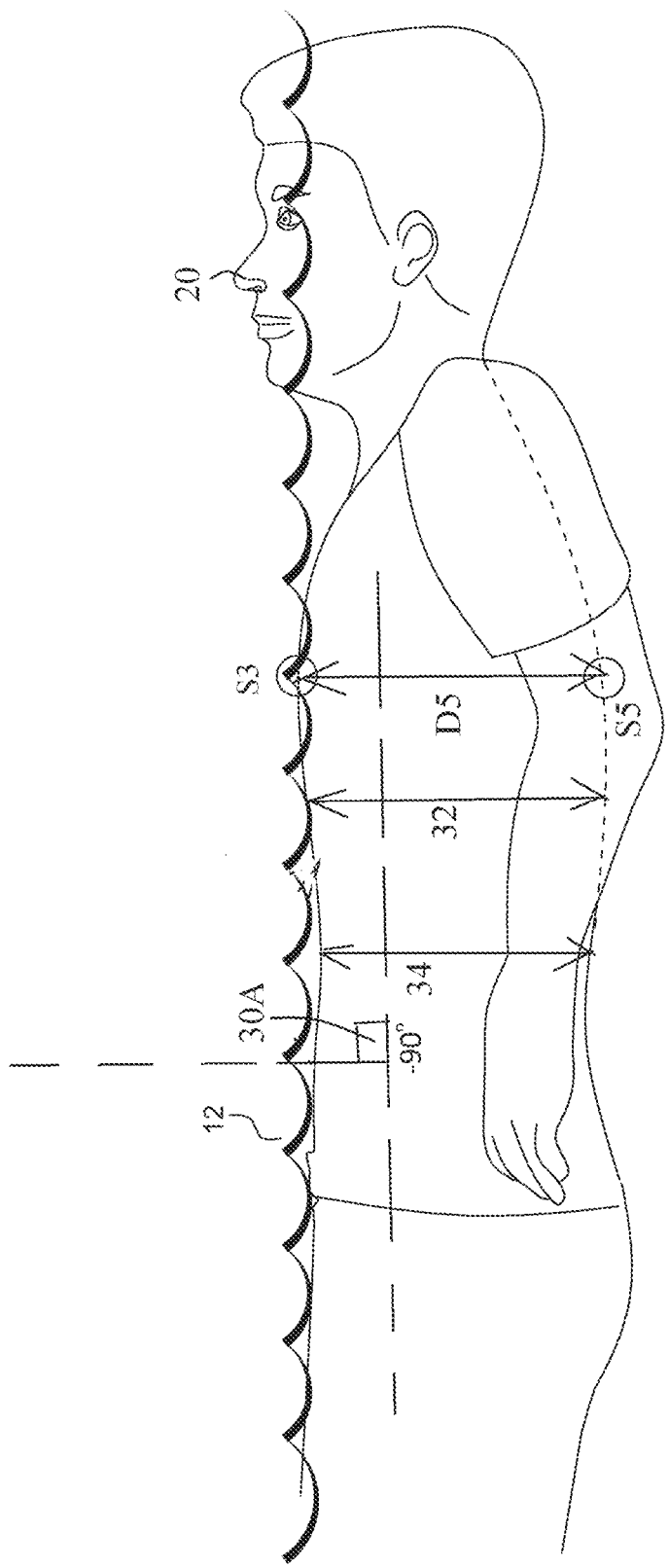
FIG. 24 is a side view of the user wearing the apparatus of FIG. 19, at (−90) degrees pitch.

FIG. 24 is a side view of the user wearing the apparatus of FIG. 19, at (−90) degrees pitch.

(−90) degrees pitch 30A, i.e., lying on the back, may be determined in case depth D5 measured by depth sensor S5 is larger than depth D0 measured by the virtual depth sensor or by depth sensor S3 or S4, and the difference 34 therebetween is the maximal of all measured cases, being the thickness 32 of the torso.

In this (−90) degrees pitch case, controller 14 (FIG. 19) determines nose 20 is disposed above water level 12 in case depth D0 is of the water level 12. This may be a second group 52B.

Figure 25:
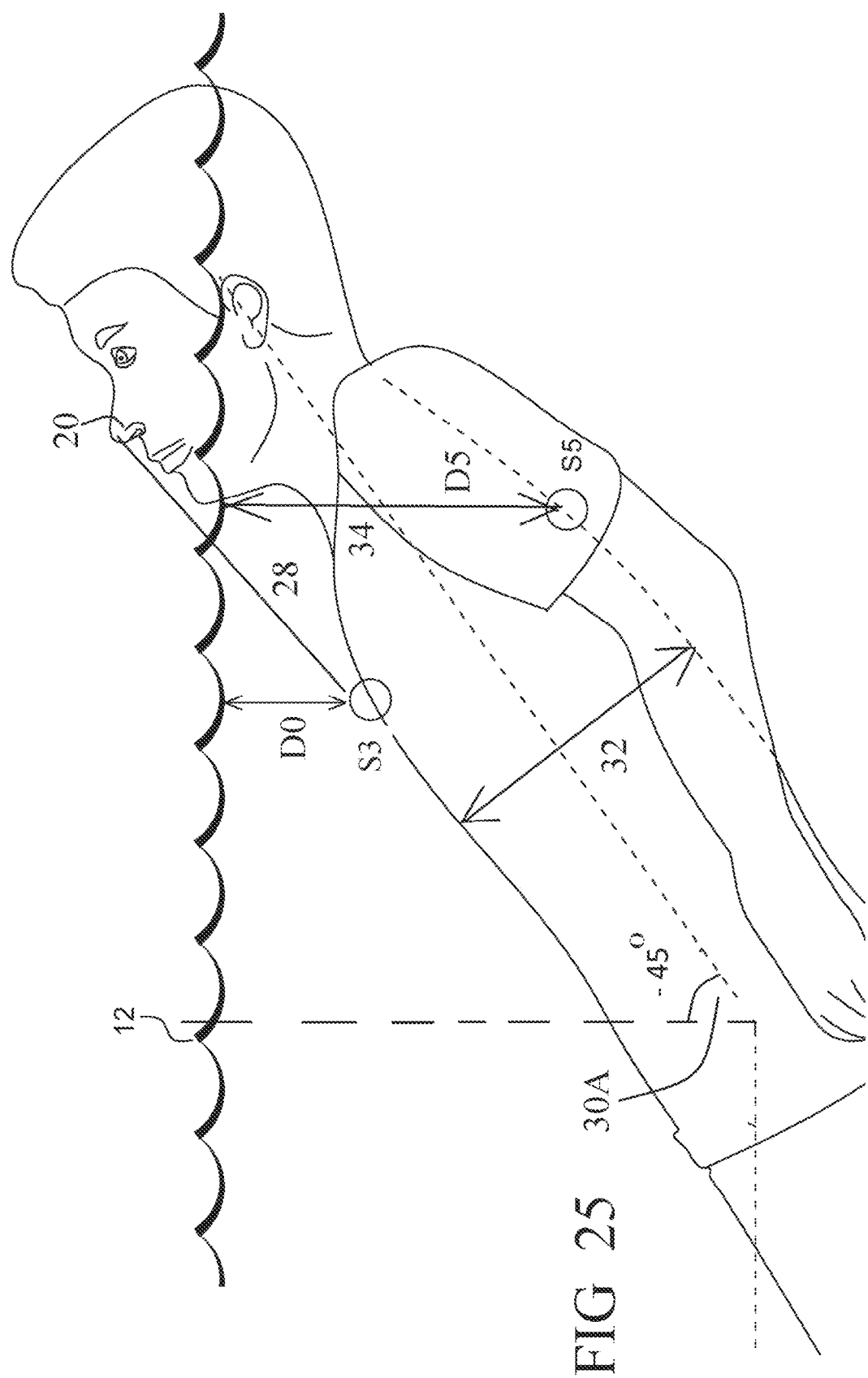
FIG. 25 is a side view of the user wearing the apparatus of FIG. 19, at (−45) degrees pitch.

FIG. 25 is a side view of the user wearing the apparatus of FIG. 19, at (−45) degrees pitch.

(−45) degrees pitch 30A, i.e., lying on the back tilted, may be determined in case depth D5 measured by depth sensor S5 like the (−90) degrees pitch is larger than depth D0 measured by the virtual depth sensor or by depth sensor S3 or S4. However, difference 34 between D0 and D5 is smaller than thickness 32 of the torso.

The exact angle of pitch may be trigonometrically calculated according to the relation as described in FIGS. 12,13, 14,15.

Group 52C may be for the (−45 degrees) or other pitch case around (−45) degrees, controller 14 (FIG. 19) determines nose 20 is disposed above water level 12 in case depth D0 is smaller than the distance 28 between by the virtual depth sensor or by depth sensor S3 or S4 and nose 20, multiplied by a fraction (sinus) calculated obtained from the (−45 degrees) or other determined angle, thus depth D0 is smaller than distance 28 of the zero angle case of FIG. 21.

Figure 26:
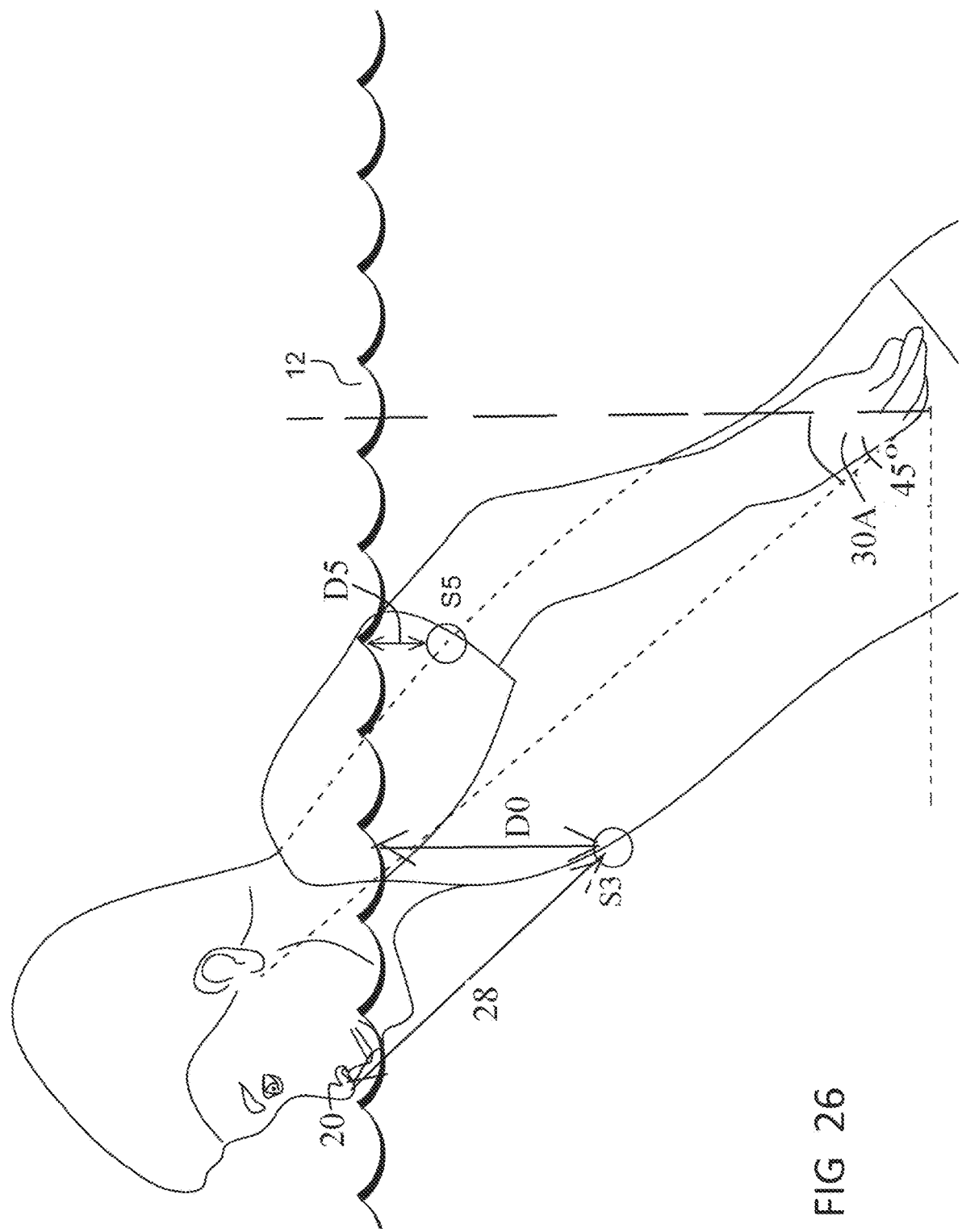
FIG. 26 is a side view of the user wearing the apparatus of FIG. 19, at 45 degrees pitch.

FIG. 26 is a side view of the user wearing the apparatus of FIG. 19, at 45 degrees pitch.

A 45 degrees pitch 30A, i.e. lying on the stomach tilted, may be determined in case depth D5 is smaller than depth D0.

The exact angle of pitch may be trigonometrically calculated according to the relation between difference 34 and thickness 32.

In the 45 degrees or other pitch case around 45 degrees, controller 14 (FIG. 19) determines nose 20 is disposed above water level 12 in case depth D5 is smaller than distance 28 between by the virtual depth sensor or by depth sensor S3 or S4 and nose 20, multiplied by a fraction (sinus) calculated obtained from the (−45 degrees) or other determined angle, thus depth D5 is smaller than distance 28.

Figure 27:
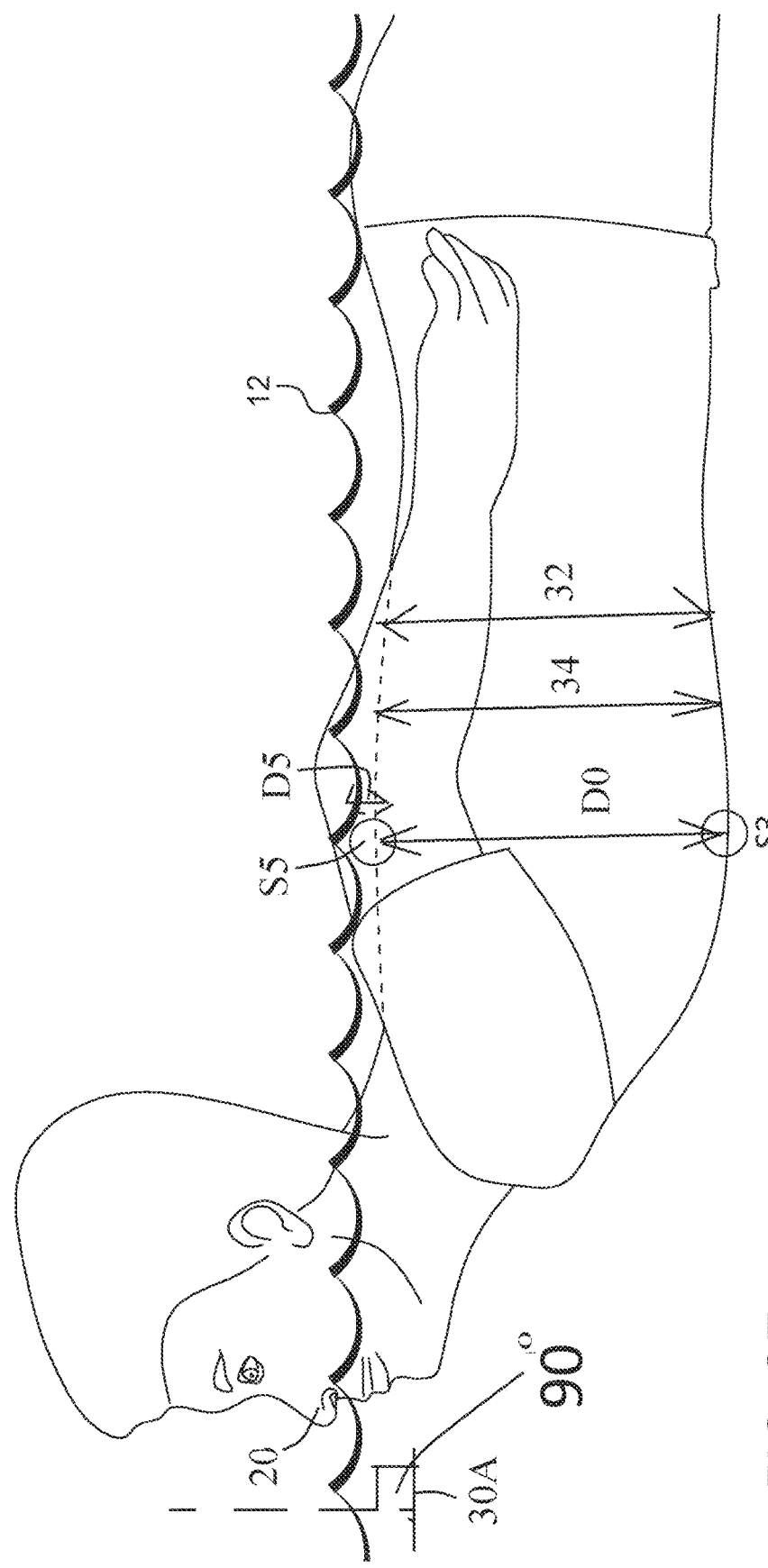
FIG. 27 is a side view of the user wearing the apparatus of FIG. 19, at (90) degrees pitch.

FIG. 27 is a side view of the user wearing the apparatus of FIG. 19, at 90 degrees pitch.

90 degrees pitch 30A, i.e. lying on the stomach not tilted, may be determined in case depth D0 larger than depth D5, and the difference 34 therebetween is the maximal of all measured cases, being the thickness 32 of the torso.

In these 90 degrees pitch case, controller 14 (FIG. 19) determines nose 20 is disposed above water level 12 in case depth D5 is of the water level 12.

The above-mentioned measurements have assumed typical positions of nose 20 in relation to the torso.

Depth and pitch measurements alone are not sufficient to ensure the above determinations, for example that for the 90 degrees pitch that nose 20 is disposed above water level 12 in case depth D5 is of the water level 12, since nose 20 might be disposed differently in relation to the torso.

Figure 28:
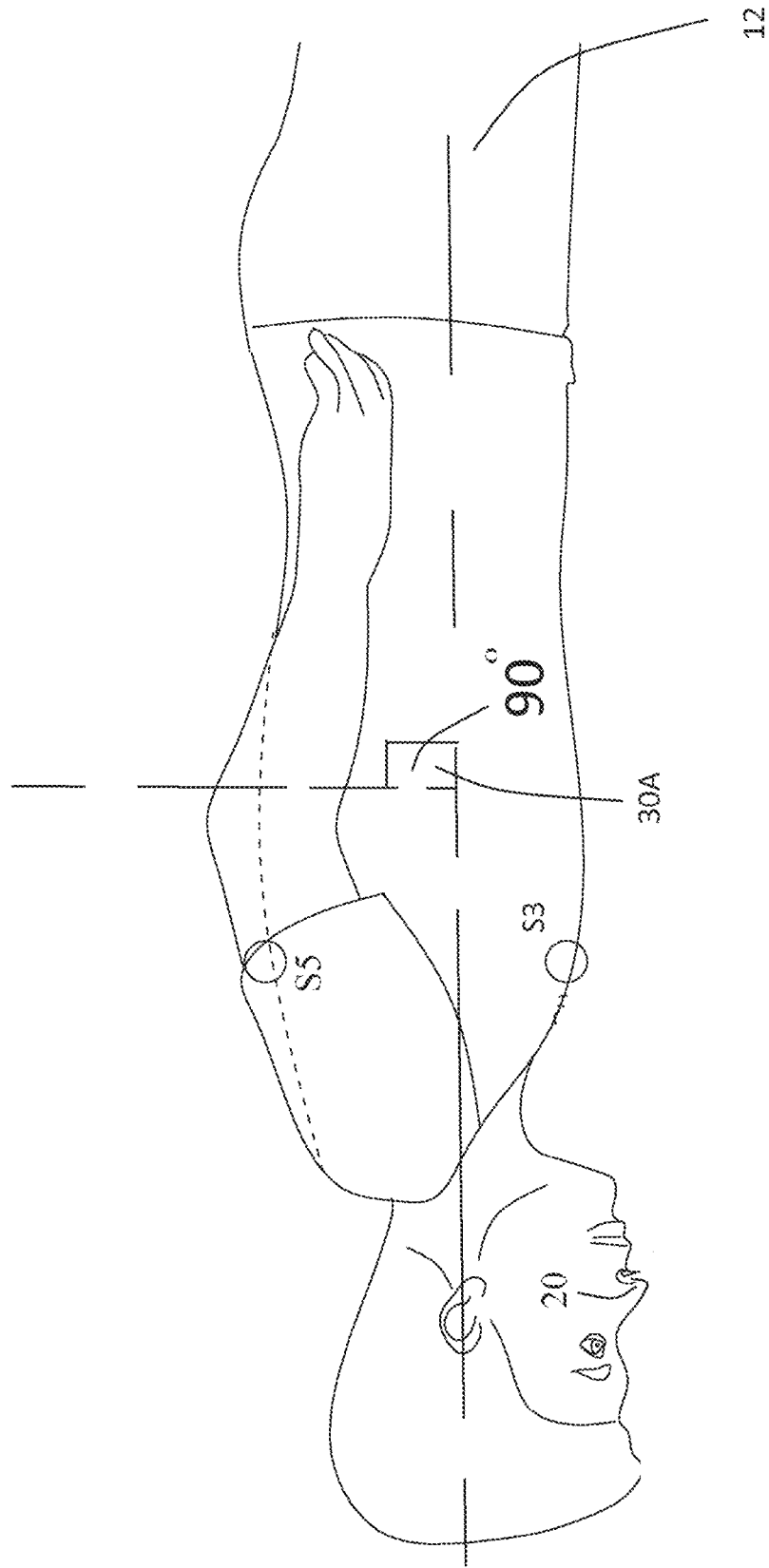
FIG. 28 is a side view of the user wearing the apparatus of FIG. 19, at a different scenario of (90) degrees pitch, being due to a different position of the nose in relation to the torso.

FIG. 28 is a side view of the user wearing the apparatus of FIG. 19, at a different scenario of 90 degrees pitch, being due to a different position of the nose in relation to the torso.

In these 90 degrees pitch case, i.e. lying on the stomach not tilted, where nose 20 is disposed lower than of FIG. 27, controller 14 (FIG. 19) must determine nose 20 is disposed below water level 12 even in case depth D0 is of the water level 12.

The above-mentioned depth, angle and motion measurements are configured for estimating whether the nose is disposed above or below water level 12.

Figure 29:
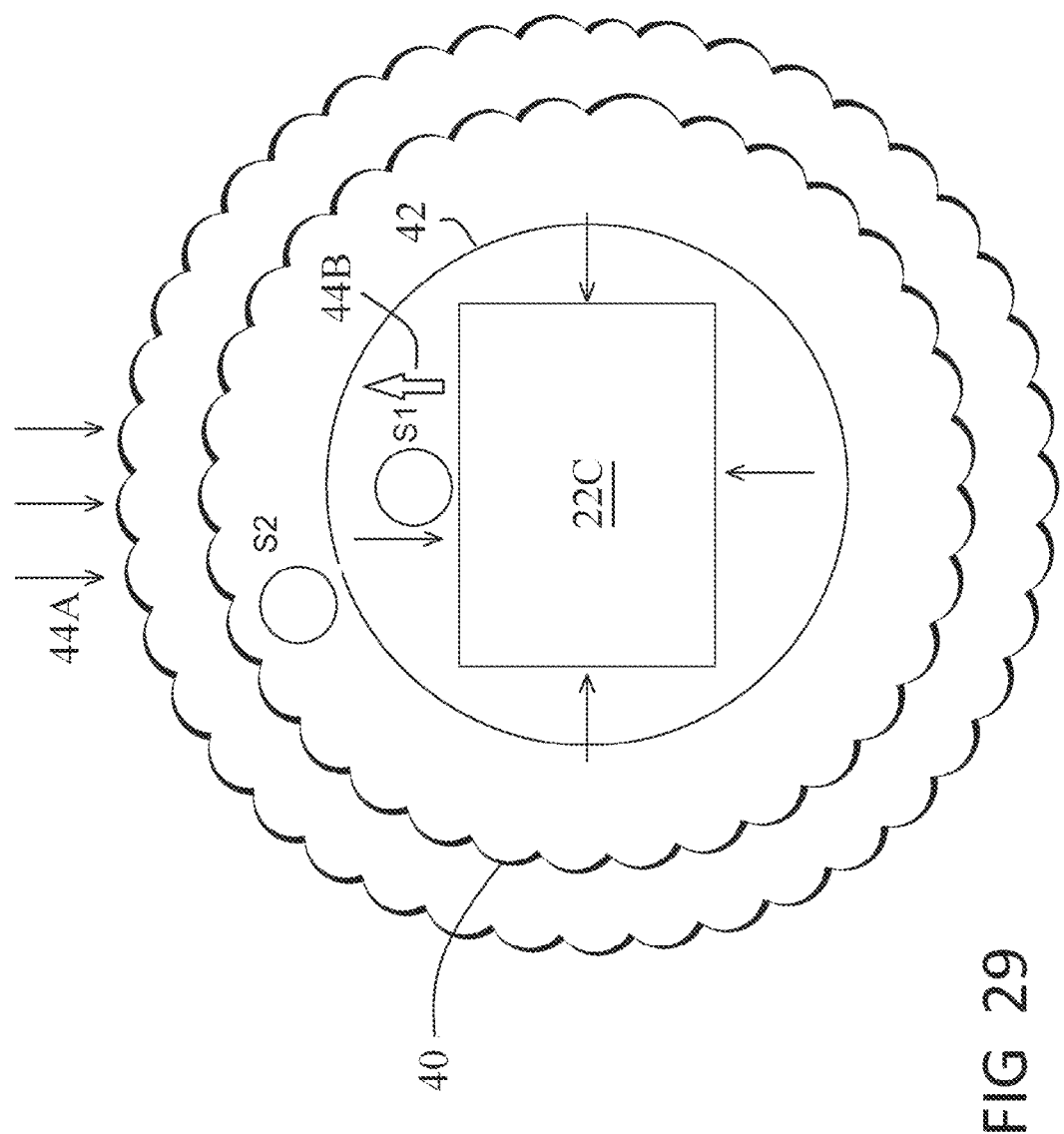
FIG. 29 is a top view of the torso wearing the apparatus of FIG. 19.

FIG. 29 is a top view of the torso wearing the apparatus of FIG. 19. Since normal swimming allows immersing the nose in the water for short periods, the above-mentioned measurements alert upon exceeding pre-determined periods.

A respiration sensor may accompany the drowning determination.

The respiration sensor may include a depth sensor S1 attached to the user's chest; and an elastic belt 42 for pressing sensor S1 to the user's chest; and a depth sensor S2 not being pressed by belt 42.

Depth sensor S2 senses water pressure 44 only, whereas depth sensor S1 senses water pressure 44A in addition to chest pressure 44B, thus allowing calculating chest pressure 44B by subtraction of S2 measurement from S1.

In the figures and/or description herein, the following reference numerals (Reference Signs List) have been mentioned:

Numeral 10 denotes the apparatus for determining drowning risk according to one embodiment of the invention;

D0: depth measured by the virtual depth sensor or by depth/pressure sensor S3 or S4;

D0': depth of by the virtual depth sensor or by depth/pressure sensor S3 or S4 written in memory 50;

D5': depth of depth/pressure sensor S5 written in memory 50;
S1,S2: depth/pressure sensors, functioning as a respiration sensor;
S3,S4,S5: depth/pressure sensors, functioning as well for measuring pitch and roll angles;
12: water level;
14: controller;
16: device such as an operable inflating device, which may include an inflatable balloon, a gas tank, and a hammer for releasing the cap of the gas tank;
18: shirt including sensors S1,S2,S3,S4,S5 and controller 14 and other elements;
20: user's nose;
22A: front of torso 22C;
22B: rear of torso 22C;
22C: torso;
24: distance between depth sensors S3 and S4;
28: actual distance between by the virtual depth sensor or by depth sensor S3 or S4 and nose 20;
28': distance between the virtual depth sensor or the depth sensor S3 or S4 and nose 20 written in memory 50;
30A: pitch measured by pitch sensor such as by the combination of by the virtual depth sensor or by depth sensor S3 combined with S5, or by the combination of depth sensors S3,S4 and S5;
30A': pitch written in memory 50;
30B: roll measured by the combination of depth/pressure sensors S3 and S4;
30B': roll written in memory 50;
32: thickness of torso 22C;
34: depth difference between depths D0 and D5;
40: water;
44A: water pressure;
44B: chest pressure applied by breathing;
50: memory;
52A: set/group of parameters written in memory, the combination thereof indicating nose 20 being disposed above the water level;
52B,52C,52D,52E,52F: other groups like 52A;
61: center between sensors S3 and S4;
63: user's toes.

What is claimed is:

1. Apparatus for detecting a drowning or swimming condition, the apparatus comprising:
three pressure sensors, for attachment to a torso of a user in water, to define a plane of the torso; and
a controller configured to receive water pressure measurements from each of the three pressure sensors and responsively to calculate an angular position of the torso plane relative to the water surface.

2. The apparatus according to claim 1, wherein the controller is further configured to calculate, from the water pressure measurements, a depth of the torso, and to determine, from the angular position of the torso plane and from the depth, whether the user's nose is above the water surface.

3. The apparatus according to claim 1, further comprising at least one additional pressure sensor secured by an elastic band to the user's chest, for measuring chest expansion, and wherein the controller is further configured to receive additional pressure measurements from the at least one additional pressure sensor and responsively to assess whether a respiration pattern of the user is normal.

4. The apparatus according to claim 1, wherein the controller is further configured for identifying patterns of known swimming styles according to depths and angular positions of the torso plane, calculated from the water pressure measurements.

5. The apparatus according to claim 1, f wherein one of the pressure sensors is attached to a top of the user's torso, at a known distance from a nose of the user, and wherein the controller is further configured to determine, from a measured depth by the pressure sensor at the top of the torso from the known distance, and from calculated torso angles, whether the user's nose is above the water surface.

6. The apparatus according to claim 5, wherein the controller is further configured to apply trigonometric formulas and parameters for determining whether the user's nose is above the water surface.

7. The apparatus of claim 1, wherein the controller is further configured to determine a depth of the torso from the water pressure measurements, and to determine a drowning condition of the user according to the depth and from the angular position of the torso.

8. The apparatus of claim 7, wherein the controller determines the drowning condition according to the depth and angular position of the torso and one or more additional factors including: a duration of time a nose and mouth of the user are immersed, a determination of whether movements of the user, indicated by the pressure measurements, resemble any known swimming styles, and respiratory regularity, based on a frequency and amplitude of the user's chest movement.

9. The apparatus of claim 8, wherein the duration of time is a continuous time or a fragmented period of time within a defined moving time frame.

10. The apparatus of claim 8, wherein the swimming styles are defined by cyclical movements of the torso.

11. The apparatus of claim 1, further comprising a shirt to be worn by the user to which the three pressure sensors and the controller are attached.

* * * * *